United States Patent [19]

Williamson

[11] 4,281,017
[45] Jul. 28, 1981

[54] PHARMACEUTICALLY ACTIVE INDANE DERIVATIVES

[75] Inventor: William R. N. Williamson, Slough, England

[73] Assignee: Lilly Industries Limited, London, England

[21] Appl. No.: 74,221

[22] Filed: Sep. 10, 1979

[30] Foreign Application Priority Data

Sep. 16, 1978 [GB] United Kingdom ............... 37121/78

[51] Int. Cl.³ .................... C07C 59/86; C07C 69/738; A61K 31/235; A61K 31/19
[52] U.S. Cl. ...................................... 424/308; 560/51; 560/81; 560/82; 562/462; 562/489; 424/317
[58] Field of Search .................... 562/462; 560/51; 424/308, 317

[56] References Cited

U.S. PATENT DOCUMENTS

| | | | |
|---|---|---|---|
| 3,558,613 | 1/1971 | Kuhn | 562/462 |
| 3,668,241 | 6/1972 | Cragoe | 562/462 |
| 3,704,314 | 11/1972 | Cragoe | 562/462 |
| 3,929,872 | 12/1975 | Cragoe | 562/462 |
| 4,007,179 | 2/1977 | Yoshida | 562/462 |
| 4,076,838 | 2/1978 | Payne | 562/462 |
| 4,088,787 | 5/1978 | Teulon | 562/462 |
| 4,096,267 | 6/1978 | Cragoe | 562/462 |

OTHER PUBLICATIONS

Chem. Abst., 86: 71,126g, (1977).

Primary Examiner—Natalie Trousof
Assistant Examiner—Michael Shippen
Attorney, Agent, or Firm—James L. Rowe

[57] ABSTRACT

Compounds of formula I

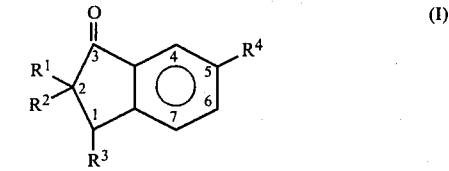

wherein either $R^1$ and $R^2$ are both hydrogen or $R^1$ and $R^2$, taken together, represent a group of formula (a):

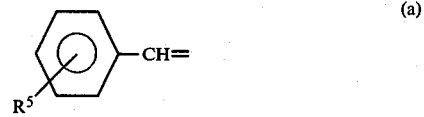

in which $R^5$ is hydrogen, halogen or $C_{1-4}$ alkyl, $R^3$ is hydrogen or a group of formula (b):

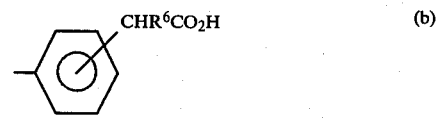

in which $R^6$ is hydrogen or $C_{1-4}$ alkyl, and $R^4$ is hydrogen or a group of formula $-CHR^7COOH$, where $R^7$ is hydrogen or $C_{1-4}$ alkyl, provided that:
(i) when $R^3$ is a group of formula (b), then $R^1$, $R^2$ and $R^4$ are all hydrogen,
(ii) when $R^3$ is hydrogen, then $R_4$ is $-CHR^7COOH$, and
(iii) when $R^1$ and $R^2$, together, represent a group of formula (a), then $R_3$ is hydrogen;

possess pharmacological activity, in particular anti-inflammatory activity and are particularly useful in treatment of rheumatoid arthritis.

7 Claims, No Drawings

PHARMACEUTICALLY ACTIVE INDANE DERIVATIVES

This invention relates to novel indane derivatives which possess useful pharmacological activity, to the use of the new compounds as pharmaceuticals, especially as anti-inflammtories, and to pharmaceutical formulations containing the new indane derivatives as an active ingredient.

According to the invention there are provided indane derivatives of formula (I):

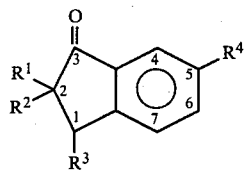
(I)

wherein either $R^1$ and $R^2$ are both hydrogen or
$R^1$ and $R^2$, taken together, represent a group of formula (a):

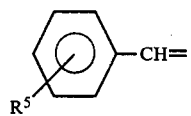
(a)

in which $R^5$ is hydrogen, halogen or $C_{1-4}$ alkyl,
$R^3$ is hydrogen or a group of formula (b):

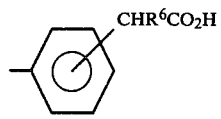
(b)

in which $R^6$ is hydrogen or $C_{1-4}$ alkyl, and
$R^4$ is hydrogen or a group of formula —CHR$^7$COOH, where $R^7$ is hydrogen or $C_{1-4}$ alkyl, provided that:
(i) when $R^3$ is a group of formula (b), then $R^1$, $R^2$ and $R^4$ are all hydrogen,
(ii) when $R^3$ is hydrogen, then $R_4$ is —CHR$^7$COOH, and
(iii) when $R^1$ and $R^2$, together, represent a group of formula (a), then $R_3$ is hydrogen; or a pharmaceutically acceptable salt or ester thereof.

Where $R_3$ is phenyl substituted by —CHR$^6$CO$_2$H, the —CHR$^6$CO$_2$H group is preferably in the para-position of the phenyl.

Where $R_1$ and $R_2$, together, represent a group of the formula (a), the $R_5$ therein is preferably in the para-position of the phenyl radical.

The preferred halogen as $R_5$ is chlorine, the preferred significance of $R_5$ being hydrogen or chlorine.

As examples of pharmaceutically acceptable salt forms of the compounds of formula (I) may be given the alkali-metal and alkaline earth metal salt forms, for example the sodium, calcium and magnesium salt forms.

As examples of pharmaceutically acceptable ester forms of the compounds of formula I may be given the $C_{1-4}$ alkyl, e.g. methyl, ethyl and n-butyl, ester forms.

As will be appreciated, where, in the compounds of formula I, $R^6$ or $R^7$ is other than hydrogen, the compounds possess a chiral centre and hence can exist in optically active enantiomeric form, in dl-form or in racemate form. The present invention is not intended to be limited to any particular form.

Compounds of formula (I) in which $R^3$ is a group of formula (b) can be prepared from compounds of formula:

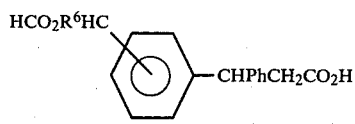

by an internal Friedel-Crafts reaction using polyphosporic acid at a temperature of approximately 100° C. The benzylidene compounds of formula:

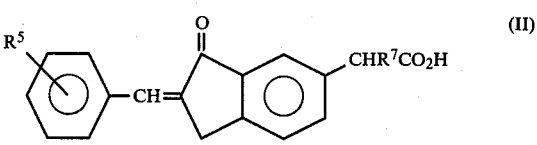
(II)

can be prepared in two ways depending on whether $R^7$ is hydrogen or $C_{1-4}$ alkyl.

Such compounds in which $R^7$ is hydrogen can be prepared from known starting materials by the following synthesis:

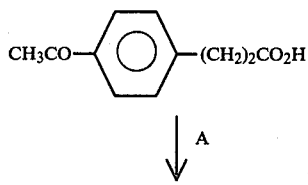

↓ A

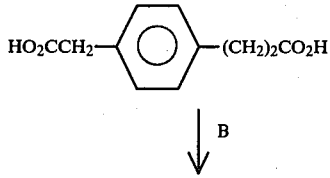

↓ B

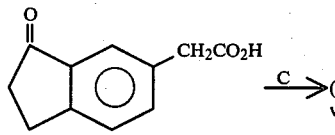
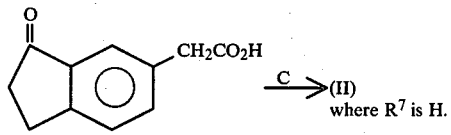
$\xrightarrow{C}$ (II) where $R^7$ is H.

Reaction A is the well-known Willgerodt-Kindler reaction. Reaction B is an internal Friedel-Crafts reaction which can be carried out with polyphosphoric acid. Reaction C is accomplished by condensation with the appropriate aldehyde of formula:

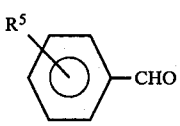

Benzylidene compounds of formula (II) in which $R^7$ is $C_{1-4}$ alkyl can be prepared by the following reaction synthesis:

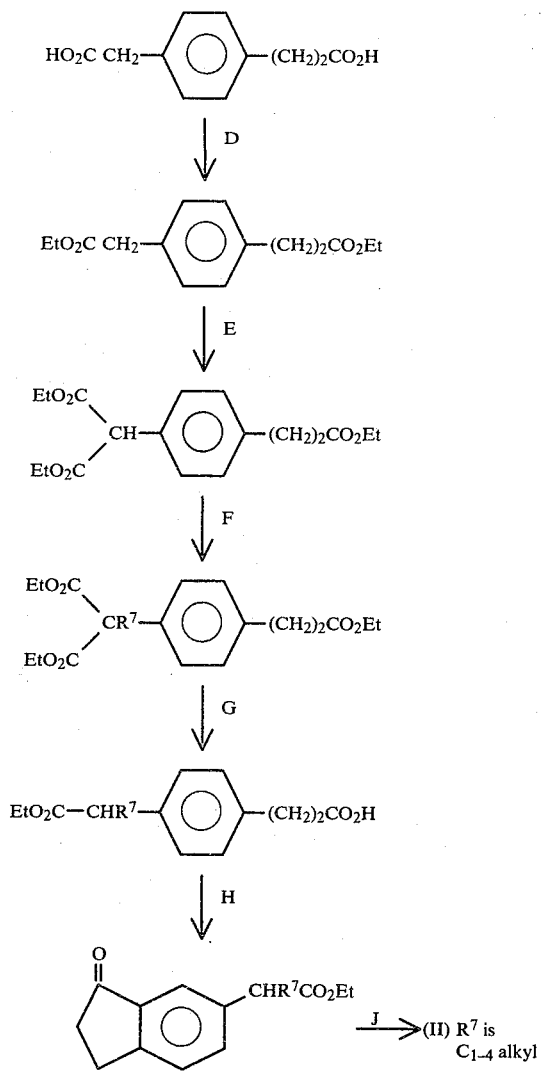

The diethyl ester was produced by reaction D by refluxing the corresponding acid in ethanol containing hydrochloric acid. The partial Claisen condensation, reaction E was accomplished using diethylcarbonate in a solution of sodium in ethanol. The alkylation reaction F can be effected using an suitable alkylating agent, preferably the corresponding iodide, by adding the triester to a warm solution of sodium in ethanol and then adding the appropriate alkyl iodide. Reaction G is a standard hydrolysis reaction and the conditions necessary to effect reaction H are similar to those necessary to effect reaction B above. Reaction J requires the pre-hydrolysis of the ethyl ester under acidic conditions followed by a condensation reaction using a similar reagent to that already specified for C above.

Compounds of formula (I) are pharmacologically active. In particular, they have been shown to have low toxicity and to possess analgesic, antipyretic and anti-inflammatory activity, particularly anti-inflammatory activity, and are particularly indicated for use in the treatment of rheumatoid arthritis.

The foregoing activities have been demonstrated in tests carried out in animals, for example in the well-known Carrageenan Test and the rat adjuvant arthritis test, usually at doses of from 0.1 to 250 mg/kg. In the treatment of humans, the dose administered may be, for example, between 1 and 25 mg/kg. but, of course, doses outside this range may be used at the discretion of the physician treating the patient. The pharmacologically active compounds of formula I may be administered by the enteral or parenteral routes and for this purpose they will normally be formulated into pharmaceutical compositions comprising the active ingredient in association with at least one pgarmaceutically acceptable carrier therefore. Such compositions form a part of this invention and will normally consist of the active ingredient mixed with a carrier, or diluted by a carrier, or enclosed or encapsulated by a carrier in the form of a capsule, sachet, cachet or other contained. The carrier may be a solid, semi-solid or liquid material which serves as a vehicle, excipient, coating agent, or medium for the active ingredient. Some examples of the carriers which may be used are lactose, dextrose, suctose, sorbitol, mannitol, starch, gum acacia, calcium photphate, liquid paraffin, cocoa butter, oil of theobroma, alginates, tragacanth, gelatin, methyl cellulose, polyoxyethylene, sorbitan monolaurate, methyl or propyl hydroxybenzoate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 1 to 1000 mg. (preferably 25 to 500 mg.) of the active ingredient. Examples of suitable dosage unit forms are tablets, hard or soft gelatin capsules, microcapsules and suppositories, as well as drug dispensing systems comprising the active ingredient contained in a flexible, imperforate polymeric material through which the drug may be released slowly by diffusion. More generally, the term "dosage unit forms" as used herein means a physically discrete unit containing the active ingredient, generally in admixture with and/or enclosed by a phramaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicyclic acid and salts thereof, caffeine, codeine phosphate, phenylbutazone, paracetamol, dextropropoxyphene and indomethacin.

The compositions of the present invention will, of course be adapted to the particular route of administration. Thus, for oral administration, tablets, pills, capsules, solutions or suspensions may be used; for parenteral administration, sterile injection solutions or suspensions may be used; for rectal administration, suppositories may be used; and for topical administration, creams, lotions or ointments may be used. Any of the foregoing compositions may, of course be formulated in delayed or sustained release from in a manner well known in the art.

The following Examples will further illustrate the preparation of the compounds of formula (I):

EXAMPLE 1

3-Oxo-5-indaneacetic acid

Polyphosphoric acid (1 kg) was stirred and heated to 95°–100° C. and 4-(2-Carboxyethyl)phenylacetic acid (100 g, 0.48 mol) added over 10 minutes. The mixture was stirred for 0.5 hours and poured into ice and H₂O; the product was continuously extracted with CHCl₃, and recrystallised from benzene to give the title product, m.p. 133°–5° C.

EXAMPLE 2

2-Benzylidene-3-oxo-5-indaneacetic acid

3-Oxo-5-indaneacetic acid (4.94 g, 0.026 mol) was added to a stirred solution of 85% KOH (3.43 g, 0.052 mol) in EtOH (73 ml) containing benzaldehyde (2.76 g, 0.026 mol) at 10° C. and stirred for 40 minutes. The potassium salt of the precipitated product was filtered off, dissolved in H₂O (100 ml) was acidified with conc. HCl to give the title product, m.p. 202°–4° C. (EtOH).

EXAMPLE 3

Similarly, 2-(p-chlorobenzylidene)-3-oxo-5-indaneacetic acid, m.p. 264°–6° C. was prepared.

EXAMPLE 4

Ethyl 4-(2-carbethoxyethyl)phenylacetate 4-(2-Carboxyethyl)phenylacetic acid (20.82 g, 0.1 mol) was refluxed overnight in EtOH (416 ml) containing conc. HCl (10.8 ml). The solvent was evaporated and the ester distilled.

EXAMPLE 5

Dietyl 4-(2-carbethoxyethyl)phenylmalonate

The diester of Example 4 (340 g, 1.29 mol) was stirred in diethyl carbonate (1975.4 g, 16.7 mol) at 80°–100° C. and treated with a solution of sodium (29.58 g, 1.29 mol) in EtOH (687 ml) and the mixture was stirred and distilled until the distillate temperature reached 123° C. After storage in a refrigerator overnight, the solution was treated with AcOH (142 ml) in H₂O (567 ml), extracted with Et₂O. The Et₂O was washed with saturated NaHCO₃ and saturated NaCl solutions, dried (Na₂SO₄), filtered and evaporated and the residue distilled to give the title product, b.p. 170° C./0.15 mm.

EXAMPLE 6

Diethyl-4-(2-carboxyethyl)methylphenylmalonate

The tricarboxylic ester produced in Example 5 (300 g, 0.89 mol) in EtOH (200 ml) was added to a warm solution of sodium (20.7 g, 0.9 mol) in EtOH (700 ml). Methyl iodide (332.5 g, 2.34 mol) was added, the solution was stirred and refluxed for 40 minutes and further MeI (322.5 g) added and then again (196.1 g, 1.4 mol) after 2 hours. After the total reflux time of 3 hours the solution was evaporated, H₂O added and the mixture extracted with Et₂O. The Et₂O solution was worked up as in Example 5 to give the title product ($n_D^{21}$ 1.4920).

EXAMPLE 7

Ethyl 4-(2-carboxyethyl)-α-methylphenylacetate

The tricarboxylic ester of Example 6 (35 g, 0.1 mol) in EtOH (400 ml) was stirred at room temperature with a solution of KOH (13.2 g of 85%, 0.2 mol) in EtOH (100 ml) for 96 hours. The mixture was evaporated to dryness. The solid foam was broken up, treated with Et₂O (200 ml) and filtered. The residue was dissolved in H₂O (100 ml), acidified with 5 N HCl to give an oil which was extracted with Et₂O. The Et₂O was dried (Na₂SO₄) filtered and evaporated to give an oily solid. The solid was shaken with a mixture of CHCl₃-light petroleum (b.p. 40°–60° C.) (100 ml of 50:50), filtered, the residue washed with the same solvent mixture (100 ml) and the filtrate evaporated to leave an oil which was distilled to give the title product, b.p. 175°–7° C./0.25 mm.

EXAMPLE 8

Using the process of Example 1, the ester of Example 7 was converted to ethyl 3-oxo-5-indane-α-methyl acetate, b.p. 137° C./0.2 mm.

EXAMPLE 9

3-Oxo-5-indane-α-methylacetic acid

The Example 8 ester (9 g, 0.038 mol) in AcOH (90 ml) was added to conc. HCl (90 ml) and kept at room temperature for 5 days. The solution was poured into H₂O (1.1) was extracted with Et₂O. The Et₂O was washed with saturated NaCl solution, dried (MgSO₄), filtered and evaporated. The product was further purified by dissolving in saturated NaHCO₃ solution (100 ml), extracting with Et₂O and acidifying the aqueous phase to give the title product, m.p. 109° C.

EXAMPLE 10

[p-(3-Oxo-1-indanyl)phenyl]acetic acid

Polyphosphoric acid (1 kg) was stirred and heated to 95°–100° C. and β-phenyl-p-(carboxymethyl)-hydrocinnamic acid (0.48 mol) added over 10 minutes. The mixture was stirred for ½ hour and poured into ice and H₂O; the title product was continuously extracted with CHCl₃ and recrystallised from ether, m.p. 151° C.

EXAMPLE 11

2-Benzylidene-3-oxo-5-indane-α-methylacetic acid

Employing the acid of Example 9 in the procedure of Example 2, above, there is obtained the title product.

EXAMPLE 12

2-(p-Chlorobenzylidene)-3-oxo-5-indane-α-methylacetic acid

Following the procedure of Example 11, above, but employing p-chlorobenzaldehyde in place of the benzaldehyde used therein, there is obtained the title product, m.p. 206°–208° C.

I claim:

1. A compound of the formula

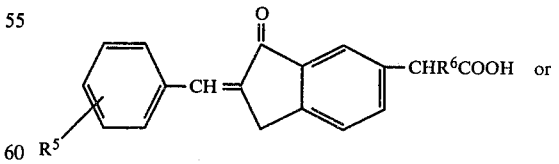

or

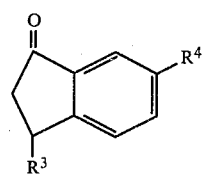

wherein
R$^3$ is;

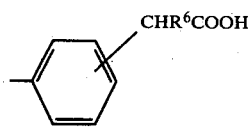

R$^4$ is H:
R$^5$ is H, halogen or (C$_1$–C$_4$)alkyl; and
R$^6$ is H or (C$_1$–C$_4$)alkyl; or a pharmaceutically acceptable salt or a (C$_1$–C$_4$)alkyl ester thereof.

2. A compound according to claim 1 wherein R$^3$ is

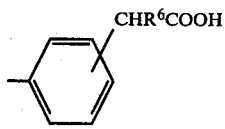

and R$^4$ is H.

3. A compound according to claim 2 in which the CHR$^6$COOH substituent in R$^3$ is in the para-position.

4. A compound according to claim 3, wherein R$^6$ is hydrogen or methyl.

5. A compound according to claim 4, wherein R$^6$ is hydrogen.

6. A compound according to claim 1 of the formula

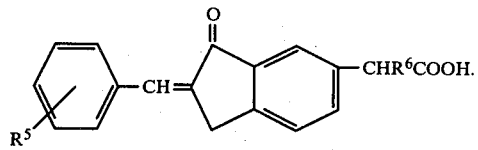

7. A pharmaceutical formulation in unit dosage form adapted for administration to treat inflammation which comprises per dosage unit an anti-inflammatorially-effective amount of a compound according to claim 6 associated with a pharmaceutically-acceptable carrier.

* * * * *